United States Patent
Zonneveld et al.

(10) Patent No.: US 9,006,521 B2
(45) Date of Patent: Apr. 14, 2015

(54) PLANT RESISTANT TO A PATHOGEN

(75) Inventors: Olaf Zonneveld, BK Enkhuizen (NL);
Michel De Lange, BK Enkhuizen (NL);
William Briggs, BK Enkhuizen (NL);
Victor Segura, Torre Pacheco/Murcia (ES)

(73) Assignee: Syngenta Participations AG, Basel (CH)

( * ) Notice: Subject to any disclaimer, the term of this patent is extended or adjusted under 35 U.S.C. 154(b) by 495 days.

(21) Appl. No.: 13/382,795

(22) PCT Filed: Jun. 30, 2010

(86) PCT No.: PCT/EP2010/059268
§ 371 (c)(1),
(2), (4) Date: Jan. 6, 2012

(87) PCT Pub. No.: WO2011/003783
PCT Pub. Date: Jan. 13, 2011

(65) Prior Publication Data
US 2012/0117683 A1    May 10, 2012

(30) Foreign Application Priority Data
Jul. 6, 2009 (EP) .................................... 09164649

(51) Int. Cl.
*A01H 5/12* (2006.01)
*C12Q 1/68* (2006.01)

(52) U.S. Cl.
CPC .............. *A01H 5/12* (2013.01); *C12Q 1/6895* (2013.01)

(58) Field of Classification Search
USPC .......................... 800/260, 267, 279, 305, 295
See application file for complete search history.

(56) References Cited

FOREIGN PATENT DOCUMENTS

| AU | 683457 | 11/1997 |
| EP | 0629343 | 12/1994 |
| JP | 6343361 | 12/1994 |

OTHER PUBLICATIONS

Jeuken M J W et al: "Efficient QTL detection for nonhost resistance in wild lettuce: backcross inbred lines versus F2 population", Theoretical and Applied Genetics; International Journal of Plant Breeding Research, Springer, Berlin, DE, vol. 116, No. 6, Feb. 2008, pp. 845-857.
Jeuken M et al: "*Lactuca saligna*, a non-host for lettuce downy mildew (*Bremia lactucae*), harbors a new race-specific Dm gene and three QTLs for resistance", Theoretical and Applied Genetics, Springer, Berlin DE, vol. 105, No. 2-3, Aug. 1, 2002, pp. 384-391.
Lebeda A et al: "Characterization of new highly virulent German isolates of *Bremia lactucae* and efficiency of resistance in wild *Lactuca* spp. germplasm", Journal of Phytopathology—Phytopathologische Zeitschrift, Wiley-Blackwell Verlag GmbH, DE, vol. 151, No. 5, May 1, 2003, pp. 274-282.
Lebeda A et al: "Histological characterization of resistance in *Lactuca saligna* to lettuce downy mildew (*Bremia lactucae*)", Physiological and Molecular Plant Pathology, vol. 44, No. 2, 1994, pp. 125-139.
Alex Beharav et al: "New Wild *Lactuca* Genetic Resources with Resistance Against *Bremia lactucae*", Genetic Resources and Crop Evolution, Kluwer Academic Publishers, DO, vol. 53, No. 3, May 1, 2006, pp. 467-474.
Bonnier F J M et al: "New Sources of Major Gene Resistance in *Lactuca* to *Bremia lactucae*", Euphytica, Kluwer Academic Press, Amsterdam, NL, vol. 61, Jan. 1, 1992, pp. 203-211.
Ales Lebeda et al: "Phenotypic and histological expression of different genetic backgrounds in interactions between lettuce, wild *Lactuca* spp., *L. sativa L. serriola* hybrids and *Bremia lactucae*", European Journal of Plant Pathology, Kluwer Academic Publishers, DO, vol. 115, No. 4, Jul. 8, 2006, pp. 431-441.
Netzer D et al: "*Lactuca saligna* L., A New Source of Resistance to Downy Mildew (*Bremia lactucae* Reg.)" Hortscience, American Society of Horticultural Science, Alexandria, VA, US, vol. 11, No. 6, Dec. 1, 1976, p. 612/613.

*Primary Examiner* — Medina A Ibrahim
(74) *Attorney, Agent, or Firm* — Karen A. Magri

(57) ABSTRACT

The present invention relates to novel *Lactuca sativa* plants resistant to *Bremia*, and to seeds of said plants. The present invention also relates to methods of making such plants and their seeds. The invention further relates to markers and the use thereof in marker assisted breeding and for identifying the *Bremia* resistance trait.

16 Claims, No Drawings

```
                        SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Forward primer for SSR-Marker NL0918

<400> SEQUENCE: 1
ccattaatcc aaaggcaac                                                  19

<210> SEQ ID NO 2
<211> LENGTH: 19
<212> TYPE: DNA
<213> ORGANISM: Artificial sequence
<220> FEATURE:
<223> OTHER INFORMATION: Revers pirmer for SSR-Marker NL0918

<400> SEQUENCE: 2
ccagtgaagg aagcaaaag                                                  19

<210> SEQ ID NO 3
<211> LENGTH: 19
<212> TYPE: DNA
<213> ORGANISM: Artificial sequence
<220> FEATURE:
<223> OTHER INFORMATION: Forward primer for SSR-Marker NL0920

<400> SEQUENCE: 3
gatggaacca ctttggatg                                                  19

<210> SEQ ID NO 4
<211> LENGTH: 19
<212> TYPE: DNA
<213> ORGANISM: Artificial sequence
<220> FEATURE:
<223> OTHER INFORMATION: Revers primer for SSR-Marker NL0920

<400> SEQUENCE: 4
cctgcaacaa gatgtgatg                                                  19
```

```
<210> SEQ ID NO 5
<211> LENGTH: 21
<212> TYPE: DNA
<213> ORGANISM: Artificial sequence
<220> FEATURE:
<223> OTHER INFORMATION: Forward primer for SNP 272 from SSR NL0918

<400> SEQUENCE: 5
attccacttg catttatctg g                                              21

<210> SEQ ID NO 6
<211> LENGTH: 21
<212> TYPE: DNA
<213> ORGANISM: Artificial sequence
<220> FEATURE:
<223> OTHER INFORMATION: Revers primer for SNP 272 from SSR NL0918

<400> SEQUENCE: 6
ccccatttga tatttcttga t                                              21

<210> SEQ ID NO 7
<211> LENGTH: 23
<212> TYPE: DNA
<213> ORGANISM: Artificial sequence
<220> FEATURE:
<223> OTHER INFORMATION: Forward primer for SNP 430 from SSR NL0920

<400> SEQUENCE: 7
tggaaagatg tgaaatccat ata                                            23

<210> SEQ ID NO 8
<211> LENGTH: 25
<212> TYPE: DNA
<213> ORGANISM: Artificial sequence
<220> FEATURE:
<223> OTHER INFORMATION: Revers primer for SNP 430 from SSR NL0920

<400> SEQUENCE: 8
gagtttcagc taagtgtaat caaat                                          25

<210> SEQ ID NO 9
<211> LENGTH: 26
<212> TYPE: DNA
<213> ORGANISM: Artificial sequence
<220> FEATURE:
<223> OTHER INFORMATION: Forward primer for SNP 305 from SSR NL0920

<400> SEQUENCE: 9
tgtgctcagt tgatataaga attagt                                         26

<210> SEQ ID NO 10
<211> LENGTH: 26
<212> TYPE: DNA
<213> ORGANISM: Artificial sequence
<220> FEATURE:
<223> OTHER INFORMATION: Revers primer for SNP 305 from SSR NL0920

<400> SEQUENCE: 10
ccaaattgga taaataaac ctacac                                          26

<210> SEQ ID NO 11
<211> LENGTH: 15
<212> TYPE: DNA
<213> ORGANISM: Artificial sequence
<220> FEATURE:
<223> OTHER INFORMATION: Probe molecule for SNP 272 (R)
```

```
<400> SEQUENCE: 11
ctacactccc acaat                                                        15

<210> SEQ ID NO 12
<211> LENGTH: 13
<212> TYPE: DNA
<213> ORGANISM: Artificial sequence
<220> FEATURE:
<223> OTHER INFORMATION: Probe molecule for SNP 272 (S)

<400> SEQUENCE: 12
actccaacaa tct                                                          13

<210> SEQ ID NO 13
<211> LENGTH: 13
<212> TYPE: DNA
<213> ORGANISM: Artificial sequence
<220> FEATURE:
<223> OTHER INFORMATION: Probe molecule for SNP 430 (R)

<400> SEQUENCE: 13
tgcagggagt taa                                                          13

<210> SEQ ID NO 14
<211> LENGTH: 14
<212> TYPE: DNA
<213> ORGANISM: Artificial sequence
<220> FEATURE:
<223> OTHER INFORMATION: Probe molecule for SNP 430 (S)

<400> SEQUENCE: 14
tgcagagagt taac                                                         14

<210> SEQ ID NO 15
<211> LENGTH: 14
<212> TYPE: DNA
<213> ORGANISM: Artificial sequence
<220> FEATURE:
<223> OTHER INFORMATION: Probe molecule for SNP 305 (R)

<400> SEQUENCE: 15
aagcatgttt cttg                                                         14

<210> SEQ ID NO 16
<211> LENGTH: 13
<212> TYPE: DNA
<213> ORGANISM: Artificial sequence
<220> FEATURE:
<223> OTHER INFORMATION: Probe molecule for SNP 305 (S)

<400> SEQUENCE: 16
agcaggtttc ttg                                                          13
```

PLANT RESISTANT TO A PATHOGEN

This application is a 371 of International Application No. PCT/EP2010/059268 filed Jun. 30, 2010, which claims priority to EP 09164649.7 filed Jul. 6, 2009, the contents of which are incorporated herein by reference.

The present invention relates to novel plants resistant to *Bremia*, and to seeds of said plants. The present invention also relates to methods of making such plants and for producing seeds thereof. The invention further relates to markers and the use thereof in marker assisted breeding and for identifying the *Bremia* resistance trait.

Downy mildew is a fungal disease caused by the fungus *Bremia lactucae*. It occurs worldwide and represents a great problem for both the yield and quality of cultivated lettuce (*Lactuca sativa*). The fungus can infect the lettuce plant at any stage of growth, after which the first symptoms of downy mildew become visible as chlorotic yellow spots on the leaf surface. Within 24-48 hours a white fluffy fungus growth becomes visible on the lower leaf surface as an indication of spore formation. During the infection the spots of lesions become increasingly larger and more chlorotic until the leaves become completely brown. Typical sporulation occurs, when lettuce seedlings are susceptible to *Bremia* downy mildew. In case plants are homozygous for the resistance trait, no sporulation is observed. When a semi-dominant resistance gene is heterozygous, also no sporulation is observed, but often yellowing or browning of cotyledons can be scored under ideal downy mildew *Bremia* incubation conditions.

*Bremia lactucae* belongs to the group Oomycetes, a class of relatively primitive fungi. Other members of this group are for instance Pythium and Phytophthora. *B. lactucae* contains different physiological species ("physio's"), is known as a very variable pathogen and is host-specific. New physio's occur relatively frequently through mutation of the avirulence genes during spore formation preceding the propagation of *B. lactucae*.

Within the genus Lactucae, to which the cultivated lettuce belongs, there are different species which are resistant to *Bremia lactucae*. The resistance is generally based on qualitative genes, known as Dm-resistance genes (Dm stands for Downy mildew). The resistance mechanism is known as gene-for-gene mechanism based on the specific interaction between products of the Dm-resistance gene and the pathogen-specific avirulence gene (HR reaction) which results in resistance of the lettuce plant. If a resistance gene is fully dominant, no *Bremia* sporulation is observed. However, if a resistance is semi-dominant, often no sporulation, but yellowing/browning of the cotyledons is observed.

Due to the high variablility of the pathogen, which is to be attributed to the occurrence of frequent mutations in the avirulence genes, the race-specific resistance mediated by the various Dm resistance genes is usually rapidly broken by newly emerging races or physios of the *Bremia* pathogen.

Because of reduced yield and quality of cultivated lettuce (*Lactuca sativa*) caused by infestation of the lettuce plant with the fungus *Bremia*, particularly *Bremia lactucae*, there is an unmet need for convenient and economically sustainable strategies to protect plants, e.g. lettuce plants like Lactuca, against *Bremia lactucae* infestation.

The present invention addresses this need by providing a *Lactuca sativa* plant, which is resistant to *Bremia lactucae* infestation and thus protected from damage caused by this pathogen. The provision of *Bremia* resistant lettuce plants is an environmentally friendly alternative for the use of pesticides and may increase the efficiency of biological control options and contribute to successful integrated pest management programs.

The technical problem underlying the present invention is, therefore, the provision of a *Bremia* resistant *Lactuca sativa* plant, which shows an improved resistance, particularly a general, race non-specific resistance to this pathogen in terms of races known as of the filing date of the present application, particularly to *Bremia* races or isoates BI1 to BI24 characterized and classified according to the SEXTET code by IBEB (International *Bremia* Evaluation Board).

The technical problem is solved by the provision of the embodiments characterized in the claims. Moreover, it was now surprisingly found within the scope of the present invention that the linkage between genes responsible for undesired, morphological changes at the plant and the gene responsible for the resistance to *Bremia lactucae* as present in the wild-type source material, is broken and thus no longer present in the *Lactuca sativa* plant according to the invention.

In a first embodiment, the present invention relates to a *Lactuca sativa* plant resistant to *Bremia lactucae*, wherein the *Bremia* resistance locus, particularly a qualitative *Bremia* resistance locus, particularly a broad-spectrum *Bremia lactucae* resistance locus, is linked to a genetic determinant and obtainable from the genome of a wild Lactuca plant, particularly from the genome of *Lactuca saligna*. In a specific embodiment of the invention, the resistance to *Bremia lactucae* is a general, race non-specific resistance.

In a further specific embodiment of the invention, the resistance trait is expressed in the *L sativa* plant without co-expression of a linked gene encoding or controlling expression of an agronomically undesirable trait such as, for example, reduced growth ("dwarfism").

In one embodiment, the present invention contemplates a plant according to any of the preceding embodiments, wherein the *Bremia lactucae* resistance locus is present in a homozygous state.

In another embodiment of the present invention, a plant according to any of the preceding embodiments is provided, wherein said *Bremia lactucae* resistance locus is located on linkage group 8.

In a further embodiment, the present invention also contemplates a plant according to any of the preceding embodiments wherein the presence of the *Bremia lactucae* resistance locus is characterized by at least one DNA marker represented by a PCR oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10 or by a pair of PCR oligonucleotide primers selected from
 a. primer pair 1 represented by a forward primer of SEQ ID NO: 1 and a reverse primer of SEQ ID NO: 2,
 b. primer pair 2 represented by a forward primer of SEQ ID NO: 3 and a reverse primer of SEQ ID NO: 4,
 c. primer pair 3 represented by a forward primer of SEQ ID NO: 5 and a reverse primer of SEQ ID NO: 6;
 d. primer pair 4 represented by a forward primer of SEQ ID NO: 7 and a reverse primer of SEQ ID NO: 8; and
 e. primer pair 5 represented by a forward primer of SEQ ID NO: 9 and a reverse primer of SEQ ID NO: 10;
or by any other marker on chromosome 8 that is statistically correlated and thus genetically linked to the *Bremia* resistance trait.

In another embodiment, the present invention also relates to a *Lactuca sativa* plant according to any of the preceding embodiments, wherein the *Bremia lactucae* resistance locus in *Lactuca saligna* is genetically linked to at least one marker locus, which co-segregates with the *Bremia* resistance trait and can be identified in a PCR reaction by at least one PCR oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10 or by a pair of PCR oligonucleotide primers selected from
  a. primer pair 1 represented by a forward primer of SEQ ID NO: 1 and a reverse primer of SEQ ID NO: 2,
  b. primer pair 2 represented by a forward primer of SEQ ID NO: 3 and a reverse primer of SEQ ID NO: 4,
  c. primer pair 3 represented by a forward primer of SEQ ID NO: 5 and a reverse primer of SEQ ID NO: 6;
  d. primer pair 4 represented by a forward primer of SEQ ID NO: 7 and a reverse primer of SEQ ID NO: 8; and
  e. primer pair 5 represented by a forward primer of SEQ ID NO: 9 and a reverse primer of SEQ ID NO: 10;
or by any other marker on chromosome 8 that is statistically correlated and thus genetically linked to the *Bremia* resistance trait.

In a further embodiment, a *Lactuca sativa* plant according to any of the preceding embodiments is provided comprising at least one allele at a qualitative trait locus in the *L. sativa* genome contributing to resistance to *Bremia lactucae*, which is genetically linked to at least one marker locus, which co-segregates with the *Bremia* resistance trait and that can be identified by at least one PCR oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10 or a pair of PCR oligonucleotide primers selected from
  a. primer pair 1 represented by a forward primer of SEQ ID NO: 1 and a reverse primer of SEQ ID NO: 2,
  b. primer pair 2 represented by a forward primer of SEQ ID NO: 3 and a reverse primer of SEQ ID NO: 4,
  c. primer pair 3 represented by a forward primer of SEQ ID NO: 5 and a reverse primer of SEQ ID NO: 6;
  d. primer pair 4 represented by a forward primer of SEQ ID NO: 7 and a reverse primer of SEQ ID NO: 8; and
  e. primer pair 5 represented by a forward primer of SEQ ID NO: 9 and a reverse primer of SEQ ID NO: 10;
or by any other marker on chromosome 8 that is statistically correlated and thus genetically linked to the *Bremia* resistance trait.

In one embodiment, said allele at the qualitative trait locus in the *L. sativa* genome contributing to resistance to *Bremia lactucae*, is obtainable from a plant which has the genetic background of *Lactuca sativa* line LSA-(1306/SAT×SAT)-37-1-3:1, particularly from a plant which has the genetic background or architecture at the qualitative trait locus of *Lactuca sativa* line LSA-(1306/SAT×SAT)-37-1-3:1, but especially from a *Lactuca sativa* line LSA-(1306/SAT×SAT)-37-1-3:1, representative seed of which is deposited at NCIMB under Accession No. NCIMB 41625, or from a progeny or an ancestor thereof comprising said qualitative trait locus.

In another embodiment as described herein, a *Lactuca sativa* plant according to any of the preceding embodiments is provided comprising at least one allele or part thereof at a qualitative trait locus in the *L. sativa* genome contributing to resistance to *Bremia lactucae*, which is complementary to the corresponding allele present in a Lactuca saligna line LSA-(1306/SAT×SAT)-37-1-3:1, deposited under Accession No. NCIMB 41625, and genetically linked to at least one marker locus within the *L saligna* genome, which co-segregates with the *Bremia* resistance trait and can be identified by at least one PCR oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10 or a pair of PCR oligonucleotide primers selected from
  a. primer pair 1 represented by a forward primer of SEQ ID NO: 1 and a reverse primer of SEQ ID NO: 2,
  b. primer pair 2 represented by a forward primer of SEQ ID NO: 3 and a reverse primer of SEQ ID NO: 4,
  c. primer pair 3 represented by a forward primer of SEQ ID NO: 5 and a reverse primer of SEQ ID NO: 6;
  d. primer pair 4 represented by a forward primer of SEQ ID NO: 7 and a reverse primer of SEQ ID NO: 8; and
  e. primer pair 5 represented by a forward primer of SEQ ID NO: 9 and a reverse primer of SEQ ID NO: 10;
or by any other marker on chromosome 8 that is statistically correlated and thus genetically linked to the *Bremia* resistance trait.

Also comprised by the present invention are primers, particularly primer pairs, but especially primer pairs consisting of forward and reverse primers exhibiting a nucleotide sequence which is at least 90%, at least 95%, at least 96%, at least 97%, at least 98%, or at least 99% identical to that given in SEQ ID NOs: 1-11, and the use thereof for identifying or characterizing the *Bremia* resistance locus.

In one embodiment of the invention oligonucleotide primers are embraced, particularly primer pairs, but especially primer pairs consisting of a forward and a reverse primer exhibiting a nucleotide sequence that hybridizes to the nucleotide sequences of the forward and reverse primer sequences given in SEQ ID NOs: 1-11, under medium, particularly under medium to high, particularly under high stringency conditions, and the use thereof for identifying or characterizing the *Bremia* resistance locus.

In one embodiment of the invention, a plant of any one of the preceding embodiments is provided, wherein primer pair 1 represented by a forward primer of SEQ ID NO: 1 and a reverse primer of SEQ ID NO: 2 and primer pair 2 represented by a forward primer of SEQ ID NO: 3 and a reverse primer of SEQ ID NO: 4 each amplifies an SSR fragment which co-segregates with the *Bremia* resistance locus, but particularly a plant, wherein
  primer pair 1 amplifies an SSR fragment of 247 bp; and
  primer pair 2 amplifies an SSR fragment of 465 bp.

In one embodiment of the invention, a plant of any one of the preceeding embodiments is provided, wherein primer pair 3 represented by a forward primer of SEQ ID NO: 5 and a reverse primer of SEQ ID NO: 6 amplifies a DNA fragment within the SSR sequence amplified by primer pair 1, comprising an SNP, particularly an SNP represented by an C for A nucleotide exchange at position 272 in the SSR sequence, which SNP co-segregates with the *Bremia* resistance locus.

In a specific embodiment of the invention, said SNP co-segregating with the *Bremia* resistance locus can be identified with a DNA probe of SEQ ID NO: 11.

In one embodiment of the invention, a plant of any one of the preceeding embodiments is provided, wherein primer pair 4 represented by a forward primer of SEQ ID NO: 7 and a reverse primer of SEQ ID NO: 8 and primer pair 5 represented by a forward primer of SEQ ID NO: 9 and a reverse primer of SEQ ID NO: 10, each amplifies a DNA fragment within the SSR sequence amplified by primer pair 2, comprising an SNP, particularly an SNP represented by a G for A nucleotide exchange at position 430 in the SSR sequence, and/or an SNP represented by a T for G nucleotide exchange at position 305 in the SSR sequence, which SNP(s) co-segregates with the *Bremia* resistance locus.

In a specific embodiment of the invention, said SNPs co-segregating with the *Bremia* resistance locus can be identified with a DNA probe of SEQ ID NO: 13 and a DNA probe of SEQ ID NO: 15, respectively.

In a further embodiment, the present invention also relates to a plant according to any of the preceding embodiments, wherein said plant is an inbred, a dihaploid or a hybrid.

In another embodiment, a plant according to any of the preceding embodiments is also contemplated, wherein said plant is male sterile.

In one aspect of the invention, the *Lactuca sativa* plant according to the invention and as described herein before is heterozygous for the *Bremia* resistance trait.

In one aspect of the invention, the *Lactuca sativa* plant according to the invention and as described herein before is homozygous for the *Bremia* resistance trait.

A specific embodiment of the invention relates to a *L. sativa* plant according to the invention and as described herein before capable of resisting infestations with *Bremia*, which plant is a plant of a cultivar group selected from butterhead, Chinese lettuce, crisphead (Iceberg forms), looseleaf, Romaine, and summer crisp.

In a further embodiment, the present invention relates to plant material obtainable from a plant according to any of the preceding embodiments including, but without being limited thereto, leaves, stems, roots, flowers or flower parts, fruits, pollen, egg cells, zygotes, seeds, cuttings, cell or tissue cultures, or any other part or product of the plant which still exhibits the resistant phenotype according to the invention, particularly when grown into a plant.

In another embodiment as described herein, plant parts of a plant according to any of the preceding embodiments are provided including, but without being limited thereto, plant seed, plant organs such as, for example, a root, stem, leaf, flower bud, or embryo, etc, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, etc; which still exhibits the resistant phenotype according to the invention, particularly when grown into a plant.

In a further embodiment of the present invention, a seed of a homozygous plant according to any of the preceding embodiments is also provided.

In another embodiment, the present invention further contemplates seeds of a Lactuca sativa plant as claimed in any of the preceding embodiments, particularly hybrid seed, comprising the genetic determinant contributing to resistance to *Bremia lactucae*.

In another embodiment, the present invention relates to seeds according to any of the preceding embodiments, deposited at the NCIMB Ltd. under Accession No. NCIMB 41625.

In a further embodiment, seeds according to any of the preceding embodiments are provided by the present invention, wherein said genetic determinant is a resistance gene located on linkage group 8.

The present invention also contemplates the use of *Lactuca sativa* of any one of the preceeding embodiments to produce seed comprising the genetic determinant contributing to resistance to *Bremia lactucae*, particularly a *Bremia* resistance gene located on linkage group 8.

In another embodiment, a kit for the detection of the *Bremia lactucae* resistance locus in *Lactuca sativa* is herein provided, wherein said kit comprises at least one PCR oligonucleotide primer, particularly a PCR oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10, or a pair of PCR oligonucleotide primers, selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10;

or any other marker on chromosome 8 that is statistically correlated and thus genetically linked to the *Bremia* resistance trait and which is able to amplify a DNA marker linked to the *Bremia lactucae* resistance locus.

In another embodiment, a kit is provided with further contains a probe molecule selected from the group consisting of SEQ ID NO: 11, SEQ ID NO: 12, SEQ ID NO: 13, SEQ ID NO: 14 and SEQ ID NO: 15.

In still another embodiment of the present invention, a DNA marker is provided that is linked to the *Bremia lactucae* resistance locus and can be amplified by at least one oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10, or by a pair of PCR oligonucleotide primers, selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10;

or by any other marker on chromosome 8 that is statistically correlated and thus genetically linked to the *Bremia* resistance trait and which is able to amplify a DNA marker linked to the *Bremia lactucae* resistance locus.

In a further embodiment, the present invention relates also to the use of some or all of these DNA markers for diagnostic selection of the lettuce *Bremia* resistance locus, particularly the Ls1 *Bremia* resistance locus, in *Lactuca sativa*.

In another embodiment, the present invention further contemplastes the use of some or all of these DNA markers for identifying in a plant the presence of the *Bremia lactucae* resistance locus and/or for monitoring the introgression of the lettuce *Bremia lactucae* resistance locus in *Lactuca sativa*.

In one embodiment, the invention relates to the polynucleotide (amplification product) obtainable in a PCR reaction involving at least one oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10, or a pair of PCR oligonucleotide primers, selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and e. primer pair 5 represented by a forward primer of SEQ ID NO: 9 and a reverse primer of SEQ ID NO: 10;

or any other marker on chromosome 8 that is statistically correlated and thus genetically linked to the *Bremia* resistance trait, which amplification product corresponds to an amplification product obtainable from *Lactuca sativa* line LSA-(1306/SAT×SAT)-37-1-3:1 (NCIMB 41625) in a PCR reaction with identical primers or primer pairs provided that the respective marker locus is still present in said *Lactuca sativa* plant and/or can be considered an allele thereof.

Also contemplated herein is a polynucleotide that has at least 90%, particularly at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the *Bremia lactucae* resistance locus.

The present invention therefore relates further in one embodiment to derived markers, particularly to derived primers or probes, developed from an amplification product according to the invention and as described herein above by methods known in the art, which derived markers are genetically linked to the *Bremia* resistance locus, particularly the Ls1 *Bremia* resistance locus, in *Lactuca sativa*.

These derived markers can then by used to identify *Bremia* resistant plants, wherein the markers specifically disclosed herein are recombined relative to the resistance and thus no longer present in the resistant plant genome.

In a further embodiment, a method is provided within the present invention for introducing at least one allele associated with resistance to *Bremia lactucae* at a qualitative trait locus contributing to resistance to *Bremia* into a *Lactuca sativa* plant lacking said allele comprising: a) obtaining a first *Lactuca sativa* plant according to any one of the preceding claims; b) crossing said first *Lactuca sativa* plant with a second *Lactuca sativa* plant, wherein said second *Lactuca sativa* plant lacks said allele; and c) identifying a plant resulting from the cross exhibiting increased resistance to *Bremia lactucae* and comprising at least one marker allele co-segregating with said *Bremia* resistance; and d) optionally, isolating said plant and e) optionally, back-crossing said plant with the first or second *Lactuca sativa* plant.

In a further embodiment, the present invention relates also to a method of obtaining a *Lactuca sativa* plant resistant against *Bremia lactucae*, comprising: a) obtaining a F1-hybrid by crossing a *Lactuca saligna* plant with a *Lactuca sativa* plant, which is sensitive to infestation with *Bremia lactucae*; b) backcrossing the F1-hybrid with said Lactuca sativa plant; and c) identifying a plant resulting from the cross exhibiting resistance to *Bremia lactucae* and comprising at least one marker allele co-segregating with said *Bremia* resistance, and d) optionally, growing said plant.

In another embodiment, a method is contemplated herein for obtaining seed according to any of the preceding embodiments comprising the steps of: a) obtaining a first *Lactuca sativa* plant according to any one of the preceding claims; b) crossing said first *Lactuca sativa* plant with a second *Lactuca sativa* plant, wherein said second Lactuca sativa plant lacks said allele; and c) identifying a plant resulting from the cross exhibiting resistance to *Bremia lactucae* and comprising at least one marker allele co-segregating with said *Bremia* resistance; and d) harvesting progeny seed from said cross comprising at least one marker allele co-segregating with said *Bremia* resistance.

In a specific embodiment of the present invention, the plant resulting from one of the above crosses is identified in step c) by applying a PCR reaction using at least one oligonucleotide primer selected from the group consisting of SEQ ID NO: 1; SEQ ID NO: 2; SEQ ID NO: 3; SEQ ID NO: 4, SEQ ID NO: 5; SEQ ID NO: 6; SEQ ID NO: 7; SEQ ID NO: 8, SEQ ID NO: 9; and SEQ ID NO: 10, or a pair of PCR oligonucleotide primers, selected from a. primer pair 1 represented by a forward primer of SEQ ID NO: 1 and a reverse primer of SEQ ID NO: 2, b. primer pair 2 represented by a forward primer of SEQ ID NO: 3 and a reverse primer of SEQ ID NO: 4, c. primer pair 3 represented by a forward primer of SEQ ID NO: 5 and a reverse primer of SEQ ID NO: 6;

d. primer pair 4 represented by a forward primer of SEQ ID NO: 7 and a reverse primer of SEQ ID NO: 8; and e. primer pair 5 represented by a forward primer of SEQ ID NO: 9 and a reverse primer of SEQ ID NO: 10;

or any other marker on chromosome 8 that is statistically correlated and thus genetically linked to the *Bremia* resistance trait.

In a specific embodiment of the invention, method step c) is further complemented by determining (a) the fragment size of the amplification product obtained in a PCR reaction with primer pair 1 and/or primer pair 2, and/or (b) the SNP in the amplicon obtained in a PCR reaction with primer pair 3, primer pair 4 and primer pair 5, using a proble molecule selected from the group consisting of SEQ ID NO: 11, SEQ ID NO: 13 and SEQ ID NO: 15.

In a further embodiment, the present invention also relates to a method according to any of the preceeding embodiments, wherein in step c) the plant resulting from any of the above crosses is identified by applying phenotypic selection based on the plants exhibiting an increased resistance to *Bremia lactucae* or by a combination of a PCR-based and a phenotypic selection.

In a further embodiment, a method of protecting a *Lactuca sativa* plant against infestation with *Bremia lactucae* is provided herein, comprising a) obtaining a Lactuca sativa plant resistant to *Bremia lactucae* according to any one of the preceeding embodiments; and b) growing said plant in an area with high disease (*Bremia lactucae*) pressure.

In another embodiment of the present invention, the use of a seed according to any one of the preceeding embodiments is contemplated for growing a *Lactuca sativa* plant resistant to *Bremia lactucae*.

Definitions

The technical terms and expressions used within the scope of this application are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A cultivated "*Lactuca sativa*" plant is understood within the scope of the invention to refer to a plant that is no longer in the natural state but has been developed by human care and for human use and/or consumption.

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

An allele associated with a qualitative trait may comprise alternative or variant forms of various genetic units including those that are identical or associated with a single gene or multiple genes or their products or even a gene disrupting or controlled by a genetic factor contributing to the phenotype represented by the locus.

As used herein, the term "marker allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breedings can be sexual or asexual, or any combination thereof. Exemplary non-limiting types of breedings include crossings, selfings, doubled haploid derivative generation, and combinations thereof.

As used herein, the phrase "established breeding population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes.

"Heterozygous" is understood within the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Genetic linkage" is understood within the scope of the invention to refer to an association of characters in inheritance due to location of genes in proximity on the same chromosome, measured by percent recombination between loci (centi-Morgan, cM).

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the term "genetic architecture at the qualitative trait locus" refers to a genomic region which is statistically correlated to the phenotypic trait of interest and represents the underlying genetic basis of the phenotypic trait of interest.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A genetic marker can be physically located in a position on a chromosome that is within or outside of the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene). In some embodiments of the presently disclosed subject matter, the one or more genetic markers comprise between one and ten markers, and in some embodiments the one or more genetic markers comprise more than ten genetic markers.

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative or qualitative trait as defined herein). Thus, in some embodiments a genotype comprises a summary of one or more alleles present within an individual at one or more genetic loci of a quantitative or qualitative trait. In some embodiments, a genotype is expressed in terms of a haplotype (defined herein below).

As used herein, the term "germ plasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the terms "hybrid", "hybrid plant," and "hybrid progeny" refers to an individual produced from genetically different parents (e.g., a genetically heterozygous or mostly heterozygous individual).

As used herein, the phrase "single cross $F_1$ hybrid" refers to an $F_1$ hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the term "dihaploid line", refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating any more (stable).

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the phrase "phenotypic trait" refers to the appearance or other detectable characteristic of an individual, resulting from the interaction of its genome, proteome and/or metabolome with the environment.

As used herein, the phrase "resistance" refers to the ability of a plant to restrict the growth and development of a specified pathogen and/or the damage they cause when compared to susceptible plants under similar environmental conditions and pathogen pressure. Resistant plants may exhibit some disease symptoms or damage under pathogen pressure, e.g. fungal pathogen pressure such as *Bremia lactucae* pathogen pressure.

As used herein, the phrase "susceptibility" refers to the inability of a plant to adequately restrict the growth and development of a specified pathogen, e.g. fungal pathogen such as *Bremia lactucae*.

As used herein, the phrase "*Bremia* resistance" or "resistance to *Bremia* races" or "*Bremia* resistant plant" refers to the plants capability to resist colonization by the fungus *Bremia lactucae*, isolates Bl:1 to Bl:24 as characterized and classified according to SEXTET code by IBEB (International *Bremia* Evaluation Board).

Resistant plants will show no or very few necroses with no or very sparse sporulation under the test conditions defined in Example 1.5 below.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower color, fruit color, and several known disease resistances such as, for example, Fungus spot resistance.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

"PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Tester" plant is understood within the scope of the invention to refer to a plant of the genus Lactuca used to characterize genetically a trait in a plant to be tested. Typically, the plant to be tested is crossed with a "tester" plant and the segregation ratio of the trait in the progeny of the cross is scored.

"Probe" as used herein refers to a group of atoms or molecules which is capable of recognising and binding to a specific target molecule or cellular structure and thus allowing detection of the target molecule or structure. Particularly, "probe" refers to a labeled DNA or RNA sequence which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, Sep. 1998 by William R. Pearson and the University of Virginia; see also W.R. Pearson (1990), Methods in Enzymology 183, 63-98, appended examples and available on workbench.sdsc.edu. For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, N.Y. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The thermal melting point is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" or "plant material obtainable from a plant" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The terms "race" or "races" refer to any inbreeding group, including taxonomic subgroups such as subspecies, taxonomically subordinate to a species and superordinate to a subrace and marked by a pre-determined profile of latent factors of hereditary traits.

The present invention relates to novel *Lactuca sativa* plants, which are resistant to *Bremia lactucae* infestation and thus protected from damage caused by this pathogen. The present invention also relates to methods of making and using such plants.

Plants according to the invention may be obtained by crossing two or more parental genotypes, at least one of which may have one or more alleles, particularly one or more alleles at corresponding qualitative trait loci contributing to Bremai resistance, which allele(s) is/are lacking in the other parental genotype or which complements the other genotype to obtain a plant according to the invention and as described herein before. If more than one qualitative trait loci contribute to the expression of the resistance trait and the two original parental genotypes do not provide the entire set of alleles, other sources can be included in the breeding population. The other parental genotype may contribute a desirable trait including crop quality demanded by the market such as, for example, increased head size and weight, higher seed yield, improved or deep green exterior color, tolerance to drought and heat and as well as improved agronomical qualities.

In iceberg lettuce, for example, desired traits comprise tight and dense head that resembles a cabbage. Iceberg lettuces are generally mild in flavour, provide a crunchy texture and exhibit a white or creamy yellow interior. Battavian lettuces are close to iceberg while being characterized by a smaller and less firm head. Regarding butter-head lettuce, these are characterized by a smaller head much more soft and oily and buttery texture. Eventually romaine lettuce has elongated upright crunchy leaves forming a loaf-shaped head with dark green outer leaves.

Beside crop quality, agronomically important characteristics such as, for example, a good plant architecture, high productivity and basic resistances to disease such as, but not limited to, Lettuce Mosaic Virus (LMV), Nasonovia, root aphids, Beet Western Yellow Virus (BMYV), Turnip Mosaic Virus (TMV) are further desired traits.

In a particular embodiment of the invention, a downy mildew resistance gene has been identified in the wild lettuce *L. saligna* accession IVT1306(=CGN05315), which confers full resistance to all known *Bremia* races to date. It was introgressed by embryo rescue in cultivated *L. sativa*. Extensive F2 and F3 population *Bremia* seedling disease tests indicated that resistance is caused by a major (semi-)dominant gene. This *L. saligna*-derived resistance ("Ls1") may be combined with other *Bremia* resistances like R17, R18, R36, R38, Dm3, Lv1 or Crapaudine.

For "Ls1" marker development two BC4F2 populations (n=70) have been developed and sampled F3 families of 70 plants per line have been tested for *Bremia* resistance using various *Bremia* strains like B120, B121, B124 and B125. BSA. Three SSR marker candidates could be identified showing specific polymorphism between R and S parental and F3 lines.

The parental genotypes may be crossed with one another to produce progeny seed. The parental genotypes may be inbred lines developed by selfing selected heterozygous plants from fields with uncontrolled or open pollination and employing recurrent selection procedures. Superior plants are selfed and selected in successive generations. In the succeeding generations the heterozygous condition gives way to homogeneous lines as a result of self-pollination and selection. With successive generations of inbreeding, the plant becomes more and more homozygous and uniform within the progeny plants. Typically, five to seven or more generations (F1 to F2; F3 to F4; F4 to F5) of selfing and pedigree selection may be practiced to obtain inbred lines that are uniform in plant and seed characteristics and that will remain uniform under continued self-fertilization.

During inbreeding, many undesirable alleles at heterozygous loci will be replaced by more favourable alleles and the unfavourable or undesired alleles eliminated from the progeny Moreover, through marker-based selection the number of favorable alleles can be maximized in that the more unfavourable alleles are identified and successively replaced by the more favorable alleles.

In one aspect, the plant according to the invention may be obtained by introgressing the *Bremia* resistance trait from an ancestor plant, particularly a wild ancestor plant into a cultivated lettuce plant, particularly a *Lactuca sativa* plant, more particularly a cultivated *Lactuca sativa* plant.

In one specific embodiment of the invention, the wild ancestor, from which the *Bremia* resistance trait may be obtained, is wild *Lactuca saligna*, particularly wild *Lactuca saligna* IVT1306(=CGN05315), or from a progeny or an ancestor thereof comprising said qualitative trait locus. The resistance trait according to the present invention, which confers to a plant expressing this trait, resistance to infestations with the fungus *Bremia lactucase*, may, in the alternative, be obtained from *Lactuca sativa* line LSA-(1306/SAT×SAT)-37-1-3:1, representative seed of which is deposited at NCIMB under Accession No. NCIMB 41625, or from a progeny or ancestor of line LSA-(1306/SAT×SAT)-37-1-3:1 comprising the *Bremia* resistance trait.

Accordingly, in a specific embodiment of the invention, the parental genotype contributing the resistance trait(s) is an inbred line having the invention relevant properties of deposited *Lactuca sativa* line LSA-(1306/SAT×SAT)-37-1-3:1, i.e. substantially the same genome architecture at the qualitative trait locus associated with *Bremia* resistance, seed samples of which have been deposited on 11 Jun. 2009 with NCIMB under accession number NCIMB 41625.

To determine the utility of the inbred line and its potential to genetically contribute to the hybrid progeny a test-cross is made with another inbred line, and the resulting progeny phenotypically evaluated.

In another specific embodiment of the invention, the parental genotype contributing to the resistance trait(s) is a hybrid having the invention relevant properties of deposited *Lactuca sativa* line LSA-(1306/SAT×SAT)-37-1-3:1, i.e. substantially the same genome architecture at the qualitative trait locus associated with *Bremia* resistance, seed samples of which have been deposited on 11 Jun. 2009 with NCIMB under accession number NCIMB 41625.

*Lactuca sativa* line LSA-(1306/SAT×SAT)-37-1-3:1 resulted from a cross of a wild *Lactuca saligna* accession IVT1306 (=CGN05315), as the donor of the resistance trait with a *Lactuca sativa* inbred line. *Bremia* resistant progeny of this cross was crossed with further inbred lines of different genetic backgrounds to finally obtain *Lactuca sativa* line LSA-(1306/SAT×SAT)-37-1-3:1.

Accordingly, *Lactuca sativa* line LSA-(1306/SAT×SAT)-37-1-3:1 or any other plant line containing the *Bremia* resistance trait may be used as a source material for introgressing said resistance trait into any desired genetic background to obtain a lettuce plant being highly resistant to infestations with the a fungus of the genus *Bremia*, more particularly to infestations with *Bremia lactucae*, may further contain one or more desirable traits such as crop quality traits demanded by the market. Beside crop quality, agronomically important characteristics such as, for example, a good plant architecture, high productivity and basic resistances to relevant pathogens such as Lettuce Mosaic Virus (LMV), Nasonovia, root aphids, Beet Western Yellow Virus (BMYV), Turnip Mosaic Virus (TMV) are further desired traits.

Based on the description of the present invention, the skilled person who is in possession of *Lactuca sativa* line LSA-(1306/SAT×SAT)-37-1-3:1, a sample of which has been deposited with NCIMB Ltd under accession number NCIMB 41625 or of a progeny or ancestor thereof containing a qualitative trait locus on linkage group 8 associated with resistance to *Bremia*, as described herein, has no difficulty to transfer the *Bremia* resistance trait of the present invention to other lettuce plants of various types using breeding techniques well-known in the art. The trait of the present invention may for example be transferred to lettuce plants of the following cultivar groups: butterhead, Chinese lettuce, crisphead (Iceberg forms), losseleaf, Romaine, summer crisp. Accordingly, in one embodiment, a plant of the present invention is a L sativa plant capable of resisting infestations with *Bremia*, which plant is a plant of the cultivar group selected from the group consisting of butterhead, Chinese lettuce, crisphead (Iceberg forms), looseleaf, Romaine, and summer crisp. In one embodiment of the invention, the lettuce plants are grown for (hybrid) seed or commercial lettuce production.

Accordingly, in another embodiment, the present invention discloses a method of transferring the *Bremia* resistance trait according to the present invention to a lettuce plant lacking said trait comprising a) obtaining a plant comprising said trait; b) crossing it to a plant lacking said trait; c) obtaining plants of the cross of step b); d) selecting a plant of step c) which is capable of resisting infestations with *Bremia* according to the present invention. In one embodiment, the method further comprises e) back-crossing a plant resulting from step d) with a lettuce plant, and f) selecting for a lettuce plant, which is capable of resisting infestations with *Bremia* according to the present invention. In one embodiment, the method further comprises obtaining an inbred lettuce plant, which is capable of resisting infestations with *Bremia* according to the present invention, and, in one embodiment, the method further comprises crossing said inbred lettuce plant to another lettuce plant to produce a hybrid lettuce plant, which is capable of resisting infestations with *Bremia* according to the present invention. In one embodiment, a lettuce plant is selected by determining presence or absence of the fungus, as described herein. In one embodiment, the plant of step a) comprising said trait is *Lactuca sativa* line LSA-(1306/SAT×SAT)-37-1-3:1, representative seed of which is deposited at NCIMB under Accession No. NCIMB 41625, or a progeny or ancestor of said plant.

In certain embodiments of the invention, a standardized Resistance Assay is used, such as that described in Example X herein below, to determine presence or absence of a resistance against *Bremia* in the progeny plants resulting from one of the above crosses and to select those progeny plants for further breeding which are resistant, to *Bremia*.

In the alternative, marker-assisted breeding may be employed to identify those individuals which contain the *Bremia* resistance locus, and/or flanking marker loci or marker loci genetically linked thereto, as described herein.

Marker-based selection may already be used in the early phases of inbred development, often in combination with screening methods which are based largely on phenotypic characteristics that can be determined visually and are related to key performance indices such as, for example, plant vigor, length of internodes, ramifications, resistance to insects or fungi, such as resistance to *Bremia* infestations, virus resistances, etc., which are relevant for the suitability of the plant to be utilized in commercial hybrid production. Selection may also be based on molecular markers, which may or may not be linked to traits of interest.

In particular, marker-based selection may be applied in combination with or followed by a phenotypic selection to identify those individuals where all of the invention relevant loci described herein before have homozygous favorable genotypes.

There are several types of molecular markers that may be used in marker-based selection including, but not limited to, restriction fragment length polymorphism (RFLP), random amplification of polymorphic DNA (RAPD), amplified restriction fragment length polymorphism (AFLP), single sequence repeats (SSR) and single nucleotide polymorphisms SNPs.

RFLP involves the use of restriction enzymes to cut chromosomal DNA at specific short restriction sites, polymorphisms result from duplications or deletions between the sites or mutations at the restriction sites.

RAPD utilizes low stringency polymerase chain reaction (PCR) amplification with single primers of arbitrary sequence to generate strain-specific arrays of anonymous DNA fragments. The method requires only tiny DNA samples and analyses a large number of polymorphic loci.

AFLP requires digestion of cellular DNA with a restriction enzyme(s) before using PCR and selective nucleotides in the primers to amplify specific fragments. With this method, using electrophoresis techniques to visualize the obtained fragments, up to 100 polymorphic loci can be measured per primer combination and only small DNA sample are required for each test.

SSR analysis is based on DNA micro-satellites (short-repeat) sequences that are widely dispersed throughout the genome of eukaryotes, which are selectively amplified to detect variations in simple sequence repeats. Only tiny DNA samples are required for an SSR analysis. SNPs use PCR extension assays that efficiently pick up point mutations. The procedure requires little DNA per sample. One or two of the above methods may be used in a typical marker-based selection breeding program.

The most preferred method of achieving amplification of nucleotide fragments that span a polymorphic region of the plant genome employs the polymerase chain reaction ("PCR") (Mullis et al., Cold Spring Harbor Symp. Quant. Biol. 51:263 273 (1986)), using primer pairs involving a forward primer and a backward primer that are capable of hybridizing to the proximal sequences that define a polymorphism in its double-stranded form.

Alternative methods may be employed to amplify fragments, such as the "Ligase Chain Reaction" ("LCR") (Barany, Proc. Natl. Acad. Sci. (U.S.A.) 88:189 193 (1991)), which uses two pairs of oligonucleotide probes to exponentially amplify a specific target. The sequences of each pair of oligonucleotides are selected to permit the pair to hybridize to abutting sequences of the same strand of the target. Such hybridization forms a substrate for a template-dependent ligase. As with PCR, the resulting products thus serve as a template in subsequent cycles and an exponential amplification of the desired sequence is obtained.

LCR can be performed with oligonucleotides having the proximal and distal sequences of the same strand of a polymorphic site. In one embodiment, either oligonucleotide will be designed to include the actual polymorphic site of the polymorphism. In such an embodiment, the reaction conditions are selected such that the oligonucleotides can be ligated together only if the target molecule either contains or lacks the specific nucleotide that is complementary to the polymorphic site present on the oligonucleotide. Alternatively, the oligonucleotides may be selected such that they do not include the polymorphic site (see, Segev, PCT Application WO 90/01069).

A further method that may alternatively be employed is the "Oligonucleotide Ligation Assay" ("OLA") (Landegren et al., Science 241:1077 1080 (1988)). The OLA protocol uses two oligonucleotides that are designed to be capable of hybridizing to abutting sequences of a single strand of a target. OLA, like LCR, is particularly suited for the detection of point mutations. Unlike LCR, however, OLA results in "linear" rather than exponential amplification of the target sequence.

Still another method that may alternatively be employed is the "Invader Assay" that uses a structure-specific flap endo-nuclease (FEN) to cleave a three-dimensional complex formed by hybridization of allele-specific overlapping oligonucleotides to target DNA containing a single nucleotide polymorphism (SNP) site. Annealing of the oligonucleotide complementary to the SNP allele in the target molecule triggers the cleavage of the oligonucleotide by cleavase, a thermostable FEN. Cleavage can be detected by several different approaches. Most commonly, the cleavage product triggers a secondary cleavage reaction on a fluorescence resonance energy transfer (FRET) cassette to release a fluorescent signal. Alternatively, the cleavage can be detected directly by use of fluorescence polarization (FP) probes, or by mass spectrometry. The invasive cleavage reaction is highly specific, has a low failure rate, and can detect zeptomol quantities of target DNA. While the assay traditionally has been used to interrogate one SNP in one sample per reaction, novel chip- or bead-based approaches have been tested to make this efficient and accurate assay adaptable to multiplexing and high-throughput SNP genotyping.

Nickerson et al. have described a nucleic acid detection assay that combines attributes of PCR and OLA (Nickerson et al., Proc. Natl. Acad. Sci. (U.S.A.) 87:8923 8927 (1990)). In this method, PCR is used to achieve the exponential amplification of target DNA, which is then detected using OLA.

Schemes based on ligation of two (or more) oligonucleotides in the presence of a nucleic acid having the sequence of the resulting "di-oligonucleotide", thereby amplifying the di-oligonucleotide, are also known (Wu et al., Genomics 4:560 569 (1989)), and may be readily adapted to the purposes of the present invention.

In one embodiment, a molecular marker is a DNA fragment amplified by PCR, e.g. a SSR marker or a RAPD marker. In one embodiment, the presence or absence of an amplified DNA fragment is indicative of the presence or absence of the trait itself or of a particular allele of the trait. In one embodiment, a difference in the length of an amplified DNA fragment is indicative of the presence of a particular allele of a trait, and thus enables to distinguish between different alleles of a trait.

In a specific embodiment of the invention simple sequence repeat (SSR) markers are used to identify invention-relevant alleles in the parent plants and/or the ancestors thereof, as well as in the progeny plants resulting from a cross of said parent plants. Simple sequence repeats are short, repeated DNA sequences and present in the genomes of all eukaryotes and consists of several to over a hundred repeats of a given nucleotide motif. Since the number of repeats present at a particular location in the genome often differs among plants, SSRs can be analyzed to determine the absence or presence of specific alleles.

In another embodiment of the invention SNP markers are used to identify invention-relevant alleles in the parent plants and/or the ancestors thereof, as well as in the progeny plants resulting from a cross of said parent plants.

In the present invention a marker or a set of two or more markers may be used comprising a pair of PCR oligonucleotide primers consisting of a forward primer and a reverse primer selected from the group of primer pair 1 represented by a forward primer of SEQ ID NO: 1 and a reverse primer of SEQ ID NO: 2 and primer pair 2 represented by a forward primer of SEQ ID NO: 3 and a reverse primer of SEQ ID NO:

4, which primers lead to an amplification product in a PCR reaction exhibiting a molecular weight or a nucleotide sequence, which is essentially identical or can be considered as an allele to that of a corresponding PCR amplification product obtainable from *Lactuca sativa* line LSA-(1306/SAT×SAT)-37-1-3:1 in a PCR reaction with the identical primer pair(s).

In a first step, DNA or cDNA samples are obtained from suitable plant material such as leaf tissue by extracting DNA or RNA using known techniques. Primers that flank a region containing SSRs within the invention-relevant qualitative trait locus disclosed herein before or within a region linked thereto, are then used to amplify the DNA sample using the polymerase chain reaction (PCR) method well-known to those skilled in the art.

Basically, the method of PCR amplification involves use of a primer or a pair of primers comprising two short oligonucleotide primer sequences flanking the DNA segment to be amplified or adapter sequences ligated to said DNA segment. Repeated cycles of heating and denaturation of the DNA are followed by annealing of the primers to their complementary sequences at low temperatures, and extension of the annealed primers with DNA polymerase. The primers hybridize to opposite strands of the DNA target sequences. Hybridization refers to annealing of complementary DNA strands, where complementary refers to the sequence of the nucleotides such that the nucleotides of one strand can bond with the nucleotides on the opposite strand to form double stranded structures. The primers are oriented so that DNA synthesis by the polymerase proceeds bidirectionally across the nucleotide sequence between the primers. This procedure effectively doubles the amount of that DNA segment in one cycle. Because the PCR products are complementary to, and capable of binding to, the primers, each successive cycle doubles the amount of DNA synthesized in the previous cycle. The result of this procedure is exponential accumulation of a specific target fragment, that is approximately $2<n>$, where n is the number of cycles.

Through PCR amplification millions of copies of the DNA segment flanked by the primers are made. Differences in the number of repeated sequences or insertions or deletions in the region flanking said repeats, which are located between the flanking primers in different alleles are reflected in length variations of the amplified DNA fragments. These variations can be detected, for example, by electrophoretically separating the amplified DNA fragments on gels or by using capillary sequencer. By analyzing the gel or profile, it can be determined whether the plant contains the desired allele in a homozygous or heterozygous state or whether the desired or undesired allele is absent from the plant genome.

In the alternative, the presence or absence of the desired allele may be determined by real-time PCR using double-stranded DNA dyes or the fluorescent reporter probe method.

Marker analysis can be done early in plant development using DNA samples extracted from leaf tissue of very young plants or from seed. This allows to identify plants with a desirable genetic make-up early in the breeding cycle and to discard plants that do not contain the desired, invention-relevant alleles prior to pollination thus reducing the size of the breeding population and reducing the requirements of phenotyping.

Further, by using molecular markers, a distinction can be made between homozygous plants that carry two copies of the desired, invention-relevant allele at the *Bremia* resistance qualitative locus and heterozygous plants that carry only one copy and plants that do not contain any copy of the favourable allele(s).

Thus, alternative markers can therefore be developed by methods known to the skilled person and used to identify and select plants with an allele or a set of alleles of a qualitative trait locus or loci according to the present invention and as disclosed herein before.

For example, the nucleotide sequence of the amplification product obtained in PCR amplification using the a pair of PCR oligonucleotide primers consisting of a forward primer and a reverse primer selected from the group of primer pair 1 represented by a forward primer of SEQ ID NO: 1 and a reverse primer of SEQ ID NO: 2 and primer pair 2 represented by a forward primer of SEQ ID NO: 3 and a reverse primer of SEQ ID NO: 4, can be obtained by those skilled in the art and new primers or primer pairs designed based on the newly determined nucleotide sequence of the PCR amplification product. Furthermore, the markers according to the invention and disclosed herein before could be positioned on a genetic map of lettuce or other species, in particular species of the family Asteraceae and known markers mapping in the same or homolog or ortholog region(s) could be used as starting point for developing new markers.

Accordingly, the markers specifically disclosed in the present invention may also be used in the identification and/or development of new or additional markers associated with the *Bremia* resistance qualitative locus, which in turn can then be used in marker assisted breeding and/or the search of recombinants flanking the *Bremia* resistance locus, and/or fine-mapping, and/or cloning of the *Bremia* resistance qualitative locus.

There are several methods or approaches available, known to those skilled in the art, which can be used to identify and/or develop markers in linkage disequilibrium and/or linked to and/or located in the region of interest, as well as markers that represent the actual causal mutations underlying the qualitative trait. Without being fully exhaustive some approaches, known by those skilled in the art, include:

use of disclosed sequences/markers in hybridization approaches to identify other sequence in the region of interest: primer sequences as disclosed herein and/or marker/gene sequences (or part thereof) that can be determined using the primer sequences as disclosed herein may be used as (hybridization) probes in isolating nucleic acid sequences/genes flanking the markers and/or linked and/or associated and/or specific for the *Bremia* resistance locus from a genomic nucleic acid sample and/or RNA or cDNA sample or pool of samples (for example screening of genomic resources like BAC libraries or gDNA or cDNA library screening).

use of disclosed sequences/markers in PCR approaches to identify other sequence in the region of interest: primer sequences as disclosed herein and/or marker/-(candidate)gene sequences (or part thereof) that can be determined using the primer sequences as disclosed may be used as (PCR) amplification primers to amplify a nucleic acid sequence/gene flanking and/or linked to and/or associated with and/or specific for the region of the *Bremia* resistance locus from a genomic nucleic acid sample and/or RNA or cDNA sample or pool of samples either or not isolated from a specific plant tissue and/or after specific treatment of the plant and from capsicum or in principal any other organism with sufficient homology.

use of disclosed sequences/markers in PCR approaches to identify other sequence in the region of interest: the nucleotide sequences/genes of one or more markers can be determined after internal primers for said marker sequences may be designed and used to further determine additional flanking sequence/genes within the region of the *Bremia* resistance locus and/or genetically linked and/or associated with the trait.

use of disclosed sequences/markers in mapping and/or comparative mapping approaches to identify markers in the same region(s) (positioning of the *Bremia* resistance locus on other maps): based on positional information and/or marker information as disclosed herein, markers, of any type, may be identified by genetic mapping approaches, eventually (if already needed) by positioning of the disclosed markers (by genetic mapping or extrapolation based on common markers across maps) on a (high density) genetic map(s), and/or integrated genetic or consensus map(s). Markers already known and/or new markers genetically linked and/or positioned in the vicinity of the disclosed markers and/or the region of the *Bremia* resistance locus may be identified and/or obtained and eventually used in (fine-) mapping and/or cloning of the *Bremia* resistance locus and/or MAS breeding applications.

use of disclosed sequences/markers in 'in-siloco' approaches to identify additional sequences/markers/(candidate) genes: Primer sequences as disclosed herein and/or marker/(candidate)gene sequences (or part thereof) that can be determined using the primer sequences as disclosed herein or based on linked markers may be used in 'in-silico' methods to search sequence or protein databases (e.g. BLAST) for (additional) flanking and/or homolog sequences/genes and/or allelic diversity (both genomic and/or cDNA sequences or even proteins and both originating from capsicum and/or any other organism) genetically linked and/or associated with the traits as described herein and/or located in the region of the *Bremia* resistance locus.

use of disclosed sequences/markers in physical mapping approaches (positioning of the *Bremia* resistance locus on physical map or genome sequence): primer sequences as disclosed herein and/or marker/gene sequences (or part thereof) that can be determined using the primer sequences as disclosed herein or using other markers genetically linked to the markers disclosed herein and/or located in the region of the *Bremia* resistance locus may be positioned on a physical map and/or (whole) genome sequence in principal of any organism with sufficient homology to identify (candidate) sequences/markers/genes applicable in (fine-mapping) and/or cloning of the *Bremia* resistance locus and/or MAS breeding applications.

use of disclosed sequences/markers to position the *Bremia* resistance locus on other (physical) maps or genomes (across species . . . for lettuce other Asteraceae species may be used as model species): primer sequences as disclosed herein and/or marker/gene sequences (or part thereof) that can be determined using the primer sequences as disclosed herein may be used in comparative genome or syntheny mapping approaches to identify homolog region and homolog and/or ortholog sequences/(candidate)genes genetically linked and/or positioned in the region of the *Bremia* resistance locus and applicable in (fine-mapping) and/or cloning of the *Bremia* resistance locus and/or MAS breeding applications.

use of disclosed sequences/markers to select the appropriate individuals allowing the identification of markers in region of interest by genetic approaches: primer sequences and/or markers as disclosed herein may be used to select individuals with different/contrasting alleles which in for example in genetic association approaches and/or bulk segregant analysis (BSA, Michelmore et al., PNAS, 88, 9828-9832, 1991) can be used to identify markers/genes in the specific region of interest and/or associated or genetically linked to the described traits.

use of disclosed information to search for (positional) candidate genes: the disclosed information may be used to identify positional and/or functional candidate genes which may be associated with the described traits and/or genetically linked.

For genotyping, mapping or association mapping, DNA is extracted from suitable plant material such as, for example, leaf tissue. In particular, bulks of leaves of a plurality of plants are collected. DNA samples are genotyped using a plurality of polymorphic SSR's, SNPs or any other suitable marker-type covering the entire lettuce genome.

Joint-analysis of genotypic and phenotypic data can be performed using standard software known to those skilled in the art. Plant introductions and germplasm can be screened for the alleles at the corresponding *Bremia* resistance locus disclosed herein, based on the nucleotide sequence(s) of the marker(s) at the marker locus/loci linked to said *Bremia* resistance locus or any other marker known to be located on chromosome 8, and the molecular weight of the allele(s) using one or more of the techniques disclosed herein or known to those skilled in the art.

The nucleic acid sequence of markers, linked markers or the *Bremia* resistance locus disclosed herein may be determined by methods known to the skilled person. For example, a nucleic acid sequence comprising said *Bremia* resistance locus or a resistance-conferring part thereof may be isolated from a *Bremia* resistant donor plant by fragmenting the genome of said plant and selecting those fragments harbouring one or more markers indicative of said *Bremia* resistance locus. Subsequently, or alternatively, the marker sequences (or parts thereof) indicative of said resistance locus may be used as (PCR) amplification primers, in order to amplify (a) nucleic acid sequence(s) comprising said resistance locus from a genomic nucleic acid sample or a genome fragment obtained from said plant. The nucleotide sequence of the *Bremia* resistance locus, and/or of any additional marker comprised therein, may be obtained by standard sequencing methods.

The present invention therefore also relates to an isolated nucleic acid (preferably DNA but not limited to DNA) sequence that comprises a *Bremia* resistance locus of the present invention, or a resistance-conferring part thereof. Thus the markers disclosed may be used for the identification and isolation of one or more markers or genes from lettuce or other vegetable crops, particularly Asteraceae crops that are linked or encode *Bremia* resistance.

The nucleotide sequence of additional markers linked to the *Bremia* resistance locus of the present invention may for instance also be resolved by determining the nucleotide sequence of one or more markers associated with the *Bremia* resistance locus and designing primers for said marker sequences that may then be used to further determine the sequence outside of said marker sequence. For example the nucleotide sequence of the SSR markers disclosed herein or any other markers predicted in the region of the *Bremia* resistance locus and/or linked to said region may be obtained by sequencing the PCR amplification product of said markers by methods well known in the art. Or alternatively using the marker sequences in a PCR or as hybridization probes to identify linked nucleotide sequences by for example, but not limited to, BAC screening.

The present invention is further described by reference to the following non-limiting examples.

EXAMPLES

Example 1

Material and Methods 1.1 Materials

Two segregating F2 and corresponding F3 populations segregating for the Ls1 *Bremia* resistance gene have been developed for BSA-mediated marker development (populations 3043=S-line [Winnie]*R-line [LSA-1306-158×K175/13×Ang-2-45)1:3-2] and population 3045=S-line [Kristo]*R-line [(Kris/B28-1-19×B06/SAT-79-6)-1-1:2]).

Sequences of SSRs candidate markers NL0918, NL0920 and NL0222, which were identified by SSR-BSA and mapped to Ls1 *Bremia* resistance genes at linkage group 8 of lettuce reference *L. sativa*×*L. serriola* RIL map.

Sequences of two EST clones LE0178 and LK1463 were obtained from UC Davis

EST collection: These 2 ESTs are located in same region as the Ls1 gene and the 3 linked SSR markers on linkage group 8.

1.2 Assay Development

All plant DNA was isolated according to the Potassium acetate+Proteinase K protocol.

For allelic sequencing up to 3 different PCR primer combinations were designed at 5' and 3' ends of linked SSRs and ESTs. PCR fragments and DNA sequences of these 5 potential markers were obtained using lines from a panel of resistant and susceptible lines.

Taqman EPR assay development was based upon discovered allele specific SNPs of the sequence panel. The EPR assay development was performed according to standard guidelines including testing of different PCR mixes, DNA concentrations and annealing temperatures. Probes are FAM- and VIC MGB Taqman probes (Eurogentec)

1.3 Assay Protocols 1.3.1 PCR Protocol

1. Isolate DNA genomic with standard DNA extraction Potassium acetate+Proteinase K protocol. Finally, 150 μl of DNA solution was obtained.
2. Dilute template DNA to 1/30;
3. Pipette 4 μl of each diluted DNA sample into individual wells.
4. Cover and centrifuge the plate and place on ice;
5. Make the master mix. Following is per reaction.

1.3.2 Taqman EPR Assay

MGB fluorescently labeled probes can be purchased from ABI. PCR amplification is performed using the following reaction mix—

| SIGMA protocol | | | |
|---|---|---|---|
| Vegetables project mix Sigma | Volume (μL) | Initial concentration | Final concentration |
| ADNg | 4 | | |
| Buffer 10x (Sigma) | 1 | 10X | |
| MgCl2 25 mM | 1.2 | 25 mM | 3 mM |
| dNTP 2.5 mM each = 10 mM all | 0.8 | 2.5 mM each | 0.2 mM each |
| Betaine 5M | 0 | 5M | 0M |
| Taq Sigma 2.5 U/μl | 0.132 | 2.5 U/μL | 0.33 U |
| VIC type probe (10 μM) | 0.1 | 10 μM | 100 nM |
| FAM probe H (10 μM) | 0.1 | 10 μM | 100 nM |
| Target Primer Foward (10 μM) | 0.2 | 10 μM | 200 nM |
| Target Primer Reverse (10 μM) | 0.2 | 10 μM | 200 nM |
| ROX 50X | 0.1 | 50X | 0.5X |
| Qsp H2O | 2.168 | | |
| Total Volume | 10 | | |

| AmpliTaq Gold protocol | | | |
|---|---|---|---|
| Vegetables project mix Gold | Volume (μL) | Initial concentration | Final concentration |
| ADNg | 4 | | |
| Buffer II | 1 | 10X | |
| MgCl2 25 mM | 1.2 | 25 mM | 3 mM |
| dNTP 2.5 mM each = 10 mM all | 0.8 | 2.5 mM each | 0.2 mM each |
| Betaine 5M | 0 | 5M | 0M |
| Gold 5 U/μl | 0.066 | 5 U/μL | 0.33 U |
| VIC type probe (10 μM) | 0.1 | 10 μM | 100 nM |
| FAM probe H (10 μM) | 0.1 | 10 μM | 100 nM |
| Target Primer Foward (10 μM) | 0.2 | 10 μM | 200 nM |
| Target Primer Reverse (10 μM) | 0.2 | 10 μM | 200 nM |
| ROX 50X | 0.1 | 50X | 0.5X |
| Qsp H2O | 2.234 | | |
| Total Volume | 10 | | |

6. Add 60 master mix to each DNA sample (everything but template DNA).
7. Spin down briefly;
8. Load the plate on PCR machine.
9. PCR program on ABI GENEAMP PCR 9700-384 plate format as follows:

$$2 \text{ min } 94°\text{ C.}$$

$$\left.\begin{array}{l} 15 \text{ sec } 94° \text{ C.} \\ 1 \text{ min } 60° \text{ C.} \end{array}\right\} 40\times$$

$$5 \text{ min } 72° \text{ C.}$$

SNP results were read on an ABI7900.

10. Read the plate at ABI7900.

1.4 Verification Panel

Verification was performed at:
(i) Specific verification panel consisting of 29 genotypes (13 fixed resistant, 15 susceptible and 1 segregating line)
(ii) 96 susceptible genotypes (cultivars)

1.5 Disease Test

The tests are done in a Climate chamber with high humidity. Day length is 16 hours and during the day the temperature is 18° C. and RH about 85%. During the night the temperature is 15° C. and the RH round 100%. Before inoculation of a test the spores of the *Bremia* pathogen are multiplied on susceptible varieties. The choice of a susceptible variety for a *Bremia* isolate is made from the official differential host set and from an internal set. Disease testing for *Bremia* resistance was performed using various *Bremia* strains or isolates like B120, B121, B124 and B125.

*Bremia* isolates are characterized and classified according to SEXTET code by IBEB (International *Bremia* Evaluation Board).

| Race | Sextet code |
| --- | --- |
| BI: 1 | 11-58-00-00 |
| BI: 2 | 63-58-00-01 |
| BI: 3 | 56-59-01-00 |
| BI: 4 | 27-59-00-00 |
| BI: 5 | 05-27-01-00 |
| BI: 6 | 27-62-00-00 |
| BI: 7 | 47-59-00-00 |
| BI: 10 | 63-59-00-00 |
| BI: 11 | 57-59-03-00 |
| BI: 12 | 57-63-03-00 |
| BI: 13 | 21-63-00-00 |
| BI: 14 | 63-62-00-00 |
| BI: 15 | 31-31-00-00 |
| BI: 16 | 63-31-02-00 |
| BI: 17 | 22-59-41-00 |
| BI: 18 | 59-31-10-00 |
| BI: 19 | 63-62-00-01 |
| BI: 20 | 63-31-10-00 |
| BI: 21 | 63-31-51-00 |
| BI: 22 | 59-63-09-00 |
| BI: 23 | 63-31-02-01 |
| BI: 24 | 59-31-10-01 |
| BI: 25 | 59-31-42-00 |
| BI: 26 | 63-31-58-01 |

Before inoculation of test material we harvest the leaves with spores and rinse the spores from the leaves with water. The concentration of the spore suspension is adjusted to 100.000 spores per ml. The spore suspension is sprayed over 1 week old plants (on cotyledons). 7 to 10 days after inoculation the observation/selection can be done. In general the cotyledons of the susceptible plants are fully covered with spores. Depending on the *Bremia* isolate used the cotyledons of the resistant plants will show nothing or a little necrosei with no or very sparse sporulation.

Example 2

Brief Breeding History of cv. (LSA-1306/SAT×SAT)-37-1-3:1-

| Female | Male | | |
| --- | --- | --- | --- |
| LSA-1306 ......x................ | SATIVA | 1996 | |
| | F1... x....... | SATIVA | 1997 |
| | BC1 F1 | | 1998 |
| | BC1 F2 | | 1999  252 single plant selections |
| | BC1 F3 | | 2000  453 single plant selections |
| | BC1 F4 | | 2001  113 single plant selections |
| | BC1 F5 | | 2002  Selection of breeding line (LSA-1306/ SATXSAT)-37-1-3:1- |

Breeding line (LSA-1306/SAT×SAT)-37-1-3:1- originated in 1996 as the result of a cross of LSA-1306=IVT1306 with a *Lactuca sativa* plant. The goal was to obtain a breeding line combining agronomic traits and downy mildew resistance coming from IVT1306 as a donor to extend breeding to all main segments (romaine, iceberg, Batavia, oak leaf and butterhead lettuce).

Before starting pedigree selection in 1998, a first backcrossing cycle was made to introduce the *Bremia* resistance factor from IVT1306 (=CGN05315: wild *Lactuca saligna* originating from Israel. Donor Institute: Instituut voor de Veredeling van Tuinbouwgewassen, Wageningen, Netherlands.) that gives resistance to all *Bremia* official races until the date published by IBEB.

BC1F2 seed was planted in 1999 and the seedlings were inoculated with *Bremia* and resistant plants blindly multiplied to go to F3.

BC1F3 seed was collected individually from the BC1F2 plant selections in 2000. Each F3 was sown and inoculated again with *Bremia*. Only F3 lines homozygous for the resistance were continued. Selections on these homozygous F3 were done in terms of the best agronomical value shown in the open field.

Selections in BC1F4 were done in 2001 in open field according to the best agronomical traits in homozygous resistant F3.

The most uniform BC1F5 combining desirable agronomic traits and *Bremia* resistance was selected in 2002.

The breeding method employed was pedigree selection, using single plant selection and mass selection practices.

Example 3

Marker Candidate Identification

Standard SSR-BSA was performed using 400 polymorphic amplifiable SSRs: the individual resistant and susceptible BSA bulks consisted of 8 F3 lines with four pooled individuals/line obtained from the 2 marker development populations 3043 and 3045. Two SSRs (NL0918 and NL0920) were identified, which are linked to the Ls1 resistance gene. The linkage was confirmed by testing individual F3 bulk member plants.

Genotyping of the corresponding "mother" F2 populations 3043 and 3045 showed perfect linkage (0 cM) with the fixed (R and S) F2 plants and up to 80% linkage with heterozygous F2 plants (of which derived F3 lines do segregate for resistance). Lower correlation in heterozygous plants can be explained in part by less reliable *Bremia* disease tests at segregating F3 populations as other Dm resistance genes in the background disturb proper *Bremia* phenotyping. *Bremia* F3 re-testing using 4 different specific *Bremia* races like B120, B121, B124 and B125 confirm close linkage of 1-2 cM. RR, SS and HR is describing the resistance gene genotype (homozygous resistant, homozygous susceptible and heterozygous resistant, respectively), while R, S and I described the disease test observations (resistant, susceptible and intermediate resistant, respectively).

Testing the specific verification panel with these 3 SSRs at ABI7330 polyacrylamide fluorescent sequencer, showed unique alleles for all resistant lines (see table 2). These "R-alleles" are never present in tested susceptible lines which show different unique alleles. These verification data (extended with 96 susceptible lines) clearly demonstrate that these 3 SSR markers show R- and S-allele specificity, potentially allowing development of co-dominant Taqman markers generally applicable in the lettuce germplasm.

Mutual close linkage of the two SSRs (NL0918 and NL0920) was confirmed to be within 2 cM on linkage group 8 by mapping with RIL lines from the *L. sativa* cv. Salinas**L. serriola* UC23US public reference population. This positions the Ls1 *Bremia* resistance gene on linkage group 8.

Sequences of the 2 SSR candidate markers and 2 linked ESTs were used for Assay Development for co-dominant Taqman marker development.

TABLE 1

Primer Sequence for SSR Markers

| SSR Marker | Primers | Fragment Size |
|---|---|---|
| NL0918 | Forward (SEQ ID NO: 1)<br>5' CCATTAATCCAAAGGCAAC 3' | Resistant:<br>247 bp |
|  | Revers (SEQ ID NO: 2)<br>5' CCAGTGAAGGAAGCAAAAG 3' | Susceptible:<br>222-241 bp |
| NL0920 | Forward (SEQ ID NO: 3)<br>5' GATGGAACCACTTTGGATG 3' | Resistant:<br>465 bp |
|  | Revers (SEQ ID NO: 4)<br>5' CCTGCAACAAGATGTGATG 3' | Susceptible:<br>438-439 bp |

TABLE 2

Size of different alleles of NL0918 and NL920

| Marker | NL0918 | NL0920 |
|---|---|---|
| ALLELE A | A | 222 | 438-439 |
| ALLELE B | B | 231 | 465 |
| ALLELE C | C | 238 |  |
| ALLELE D | D | 241 |  |
| ALLELE E | E | 247 |  |
| ALLELE F | F |  |  |

Example 4

Assay Development

Using 4 R and 4 S lines from specific verification panel, SSR alleles have been sequenced resulting in allelic haplotyping based upon observed SNP patterns.
SSR NL0920:

R-lines show 1 haplotype (A) while S lines show 2 haplotypes: Two Taqman assays have been developed based upon SNP 305 # and 430.

SSR NL0918:

R-lines show 1 haplotype (A) as well as do the S lines (B): Two Taqman assays have been developed based upon SNPs #217 and 272. No specific amplification could be obtained with SNP 217; however, Taqman marker based upon SNP 272 shows perfect correlation with specific verification panel.

Example 5

Verification and Robustness Testing

Two developed co-dominant Taqman markers of both SSRs NL0918 and NL0920 were verified for correlation with phenotyped breeding lines.
SSR NL0918:

For SSR NL0918, the SNP #217 based Taqman marker showed no correlation with lines in both specific and global verification panel. However, the SNP #272 based Taqman marker shows full correlation with phenotypes of all lines.

Testing the Taqman protocol of NL0918 showed discriminative separation and classification of the 3 observed genotypes, homozygous resistant, heterozygous and homozygous susceptible (data not shown).
SSR NL0920:

For SSR NL0920 both the SNP #305 and 430 based Taqman markers show full correlation with the phenotypes of all lines.

Testing the Taqman protocol showed that SNP #430 gives discriminative separation and classification of the 3 observed genotypes, homozygous resistant, heterozygous, and homozygous susceptible.

Two SSR-BSA derived co-dominant Taqman PCR markers have been developed for diagnostic selection of the lettuce Ls1 *Bremia* resistance locus.

The markers discriminate the susceptible Ls1 allele from the resistant LS1 allele based upon a specific SNP-mutation in both markers.

The markers show perfect correlation with the phenotypes of the lines (both Ls1 resistant and susceptible lines) and the global panel.

Example 6

Lettuce *Bremia* LS-1 Resistance Co-dominant End Point Reading (EPR)

Three SNPs, SNP-A, SNP-B and SNP-C, were identified by bulked segregant analysis as segregating with the resistance locus. Bulks were selected by results of screening with multiple *Bremia* isolates like B120, B121, B124 and B125, tested on F3 families derived by selfing individual F2 plants from an F1 plant of a cross between the resistance source and Cobham Green, a line with no known *Bremia* resistance. Close linkage between SNP-A and the resistance locus and/or SNP-B and the resistance locus (at best 0.6 cM, but not more than 5 cM) was determined in three independent F3 populations segregating for resistance.

The following table indicates the primers and probes for the SSR and SNP markers:

| SNP Marker | Primers | Probes |
|---|---|---|
| SNP 272 from SSR NL0918 | | |
| SNP-A | Forward (SEQ ID NO: 5)<br>5' ATTCCACTTGCATTTATCTGG 3'<br>Revers (SEQ ID NO: 6)<br>5' CCCCATTTGATATTTCTTGAT 3' | Resistant (SEQ ID NO: 11):<br>FAM-CTACACTCC__C__ACAAT-<br>MGB-NFQ<br>Susceptible (SEQ ID NO: 12):<br>VIC-ACTCC__A__ACAATCT-MGB-NFQ |
| SNP 430 from SSR NL0920 | | |
| SNP-B | Forward (SEQ ID NO: 7)<br>5' TGGAAAGATGTGAAATCCATATA 3'<br>Revers (SEQ ID NO: 8)<br>5' GAGTTTCAGCTAAGTGTAATCAAAT 3' | Resistant (SEQ ID NO: 13):<br>FAM-TGCAG__G__GAGTTAA-MGB-NFQ<br>Susceptible (SEQ ID NO: 14):<br>VIC-TGCAG__A__GAGTTAAC-MGB-NFQ |
| SNP 305 from SSR NL0920 | | |
| SNP-C | Forward (SEQ ID NO: 9)<br>5' TGTGCTCAGTTGATATAAGAATTAGT 3'<br>Revers (SEQ ID NO: 10)<br>5' CCAAATTGGATAAAATAAACCTACAC 3' | Resistant (SEQ ID NO: 15):<br>FAM-__A__AGCA__T__GTTTCTTG-MGB-NFQ<br>Susceptible (SEQ ID NO: 16):<br>VIC-_AGCA__G__GTTTCTTG-MGB-NFQ |

Example 7

Line Development

The resistance from *Lactuca saligna* is linked to several undesired traits like small plants, thick cracking leaves, too dark colored leaves. By crossing *Lactuca saligna* with *Lactuca sativa* the gene is transferred to *Lactuca sativa* (normal lettuce). By backcrossing with *Lactuca sativa* and subsequent selections in the field the linkage between these undesired genes and the resistance gene was brocken.

Crosses and backcrosses with L sativa showing introgression of the trait from the source into the target L sativa.

Various *Lactuca sativa* varieties have been developed all showing introgression of the resistant allele of Ls1 from *L. saligna*

Deposit

The following seed sample of *Lactuca sativa* line LSA-(1306/SAT×SAT)-37-1-3:1 was deposited with NCIMB, Ferguson Building, Craibstone Estate, Bucksburn, Aberdeen AB21 9YA, Scotland, UK on 11, Jun. 2009 under the provisions of the Budapest Treaty in the name of Syngenta Participations AG:

| *Lactuca sativa* seed line designation | Deposition date | Accession No |
|---|---|---|
| LSA - (1306/SAT × SAT) - 37 - 1 - 3:1 | 11 Jun. 2009 | NCIMB 41625 |

Access to this deposit will be available during the pendency of the application to the Commissioner for Patents and persons determined by the Commissioner to be entitled thereto upon request. Upon granting of a patent on any claims in the application, the Applicant will make the deposit available to the public pursuant to 37 CFR §1.808. Applicant will meet the requirements of 37 CFR §1.801-1.809, including providing an indication of the viability of the sample when the deposit is made. The NCIMB deposit will be maintained in that depository, which is a public depository, for a period of 30 years, or 5 years after the last request, or for the enforceable life of the patent, whichever is longer, and will be replaced if it becomes nonviable during that period.

Embodiments of the Invention

1. *Lactuca sativa* plant resistant to *Bremia lactucae*, wherein the *Bremia* resistance locus is linked to a genetic determinant and obtainable from the genome of a wild *Lactuca* plant, particularly from the genome of *Lactuca saligna*.
2. The plant according to embodiment 1, wherein the resistance to *Bremia lactucae* is a general, race non-specific resistance.
3. The plant according to embodiments 1 or 2, wherein the genetic determinant linked to a *Bremia* resistance locus is a qualitative *Bremia* resistance locus.
4. The plant according to any of the preceding embodiments, wherein the *Bremia* resistance locus is a broad-spectrum *Bremia lactucae* resistance locus.
5. The plant according to any of the preceding embodiments, wherein the *Bremia* lactucae resistance locus is present in a homozygous state.
6. The plant according to any of the preceding embodiments, wherein said *Bremia* lactucae resistance locus is located on linkage group 8.
7. The plant according to any of the preceding embodiments, wherein the *Bremia* lactucae resistance locus is genetically linked to at least one marker locus, which co-segregates with the *Bremia* resistance trait and can be identified in a PCR reaction by amplification of a DNA fragment with a pair of PCR oligonucleotide primers selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and e. primer pair 5 represented by a forward primer of SEQ ID NO: 9 and a reverse primer of SEQ ID NO: 10;
   or by any other marker on chromosome 8 that is statistically correlated and thus genetically linked to the *Bremia* resistance trait.
8. The plant according to any of the preceding embodiments, wherein the *Bremia lactucae* resistance locus corresponds to the respective resistance locus in *Lactuca saligna*, which locus is genetically linked to at least one marker locus, which co-segregates with the *Bremia* resistance trait and can be identified in the *Lactuca saligna* genome in a PCR reaction by amplification of a DNA fragment with a pair of PCR oligonucleotide primers selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10;
   or by any other marker on chromosome 8 that is statistically correlated and thus genetically linked to the *Bremia* resistance trait.
9. The plant according to any of the preceding embodiments comprising at least one allele at a qualitative trait locus in the *L. sativa* genome contributing to resistance to *Bremia lactucae*, which is genetically linked to at least one marker locus, which co-segregates with the *Bremia* resistance trait and can be identified in the *Lactuca sativa* genome in a PCR reaction by amplification of a DNA fragment with a pair of PCR oligonucleotide primers selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10;
   or by any other marker on chromosome 8 that is statistically correlated and thus genetically linked to the *Bremia* resistance trait.
10. *Lactuca sativa* plant according to any of the preceding embodiments comprising at least one allele or part thereof at a qualitative trait locus in the *L. sativa* genome contributing to resistance to *Bremia lactucae*, which is complementary to the corresponding allele present in a *Lactuca sativa* line LSA-(1306/SAT×SAT)-37-1-3:1, representative seed of which is deposited at NCIMB under Accession No. NCIMB 41625, and genetically linked to a least one marker locus within the *L saligna* genome, which co-segregates with the *Bremia* resistance trait and can be identified in the *Lactuca saligna* genome in a PCR reaction by amplification of a DNA fragment with a pair of PCR oligonucleotide primers selected from
    a. primer pair 1 represented by a forward primer of SEQ ID NO: 1 and a reverse primer of SEQ ID NO: 2,
    b. primer pair 2 represented by a forward primer of SEQ ID NO: 3 and a reverse primer of SEQ ID NO: 4,
    c. primer pair 3 represented by a forward primer of SEQ ID NO: 5 and a reverse primer of SEQ ID NO: 6;
    d. primer pair 4 represented by a forward primer of SEQ ID NO: 7 and a reverse primer of SEQ ID NO: 8; and
    e. primer pair 5 represented by a forward primer of SEQ ID NO: 9 and a reverse primer of SEQ ID NO: 10;
    or by any other marker on chromosome 8 that is statistically correlated and thus genetically linked to the *Bremia* resistance trait.
11. The plant of any one of embodiments 7 to 10, wherein primer pair 1 and primer pair 2 each amplifies an SSR fragment which co-segregates with the *Bremia* resistance locus.
12. The plant of embodiment 11, wherein primer pair 1 amplifies an SSR fragment of 247 bp.
13. The plant of embodiment 11, wherein primer pair 2 amplifies an SSR fragment of 465 bp.
14. The plant of embodiment 11, wherein primer pair 3 amplifies a DNA fragment within the SSR sequence of embodiment 12 comprising an SNP which segregates with the *Bremia* resistance locus.
15. The plant of embodiment 11, wherein primer pair 4 and primer pair 5 each amplifies a DNA fragment within the SSR sequence of embodiment 13 comprising an SNP which segregates with the *Bremia* resistance locus.
16. The plant of embodiment 14, wherein said SNP is present in the SSR fragment amplified by primer pair 3 and represented by an C for A nucleotide exchange at position 272 in the SSR sequence.
17. The plant of embodiment 15, wherein said SNP is present in the SSR fragment amplified by primer pair 4 and represented by a G for A nucleotide exchange at position 430 in the SSR sequence.
18. The plant of embodiment 15, wherein said SNP is present in the SSR fragment amplified by primer pair 5 and represented by a T for G nucleotide exchange at position 305 in the SSR sequence.
19. The plant of embodiment 16, wherein said SNP co-segregating with the *Bremia* resistance locus can be identified with a DNA probe of SEQ ID NO: 11.
20. The plant of embodiment 17, wherein said SNP co-segregating with the *Bremia* resistance locus can be identified with a DNA probe of SEQ ID NO: 13.
21. The plant of embodiment 18, wherein said SNP co-segregating with the *Bremia* resistance locus can be identified with a DNA probe of SEQ ID NO: 15.
22. The plant according to any of the preceding embodiments, wherein said plant is an inbred, a dihaploid or a hybrid.
23. The plant according to any of the preceding embodiments, wherein said plant is male sterile.
24. Plant material obtainable from a plant according to any of the preceding embodiments including, but without being limited thereto, leaves, stems, roots, flowers or flower parts, fruits, pollen, egg cells, zygotes, seeds, cuttings, cell or tissue cultures, or any other part or product of the plant which still exhibits the resistant phenotype according to the invention, particularly when grown into a plant.
25. Plant parts of a plant according to any of the preceding embodiments including, but without being limited thereto, plant seed, plant organs such as, for example, a root, stem, leaf, flower bud, or embryo, etc, ovules, pollen microspores, plant cells, plant tissue, plant cells cultures such as, for example, protoplasts, cell culture cells, cells in plant tissues, pollen, pollen tubes, ovules, embryo sacs, zygotes and embryos at various stages of development, etc; which still exhibits the resistant phenotype according to the invention, particularly when grown into a plant.
26. Seed of a homozygous plant according to any of the preceding embodiments.

27. Seed of a *Lactuca sativa* plant according to any of the preceding embodiments, comprising the genetic determinant contributing to resistance to *Bremia lactucae*.
28. Seed according to embodiment 27, wherein said seeds are hybrid seeds.
29. Seed of any of the preceding embodiments, wherein said resistance gene is located on linkage group 8.
30. Seed according to any of the preceding embodiments, deposited at the NCIMB Ltd. under Accession No. NCIMB 41625.
31. Use of *Lactuca sativa* plant of any one of embodiments 1 to 23 to produce seed comprising the genetic determinant contributing to resistance to *Bremia lactucae*.
32. A kit for the detection of the *Bremia lactucae* resistance locus in *Lactuca sativa*, wherein said kit comprises one PCR oligonucleotide primer or a pair of PCR oligonucleotide primers, which is able to amplify a DNA marker linked to the *Bremia* lactucae resistance locus.
33. A kit according to embodiment 32, wherein said DNA maker can be amplified in a PCR reaction with a pair of PCR oligonucleotide primers selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10;
      or by any other marker on chromosome 8 that is statistically correlated and thus genetically linked to the *Bremia* resistance trait.
34. A DNA marker that is linked to the *Bremia lactucae* resistance locus and can be amplified in a PCR reaction with a pair of PCR oligonucleotide primers selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10;
      or by any other marker on chromosome 8 that is statistically correlated and thus genetically linked to the *Bremia* resistance trait.
35. Use of any one of the DNA markers according to embodiment 34 for diagnostic selection of the lettuce Ls1 *Bremia* resistance locus in *Lactuca sativa*.
36. Use of any one of the DNA markers according to embodiment 34 for identifying in a plant the presence of the *Bremia lactucae* resistance locus and/or for monitoring the introgression of the lettuce *Bremia lactucae* resistance locus in *Lactuca sativa*.
37. Polynucleotide obtainable in a PCR reaction by amplification of a DNA fragment with a pair of PCR oligonucleotide primers selected from
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10;
      or by any other marker on chromosome 8 that is statistically correlated and thus genetically linked to the *Bremia* resistance trait,
      which amplification product corresponds to an amplification product obtainable from *Lactuca sativa* line LSA-(1306/SAT×SAT)-37-1-3:1, representative seed of which is deposited at NCIMB under Accession No. NCIMB 41625, in a PCR reaction with identical primers or primer pairs provided that the respective marker locus is still present in said *Lactuca sativa* plant and/or can be considered an allele thereof.
38. A polynucleotide that has at least 90%, particularly at least 95%, particularly at least 96%, particularly at least 97%, particularly at least 98%, particularly at least 99% sequence identity with the sequence of the polynucleotide of embodiment 37.
39. A polynucleotide exhibiting a nucleotide sequence that hybridizes to the nucleotide sequences of the polynucleotide of embodiment 37.
40. A method for introducing at least one allele associated with resistance to *Bremia lactucae* at a qualitative trait locus contributing to resistance to *Bremia* into a *Lactuca sativa* plant lacking said allele comprising:
   a. obtaining a first *Lactuca sativa* plant according to any one of the preceding embodiments;
   b. crossing said first *Lactuca sativa* plant with a second *Lactuca sativa* plant, wherein said second *Lactuca sativa* plant lacks said allele; and
   c. identifying a plant resulting from the cross exhibiting increased resistance to *Bremia lactucae* and comprising at least one marker allele co-segregating with said *Bremia* resistance; and
   d. optionally, isolating said plant and
   e. optionally, back-crossing said plant with the first or second *Lactuca sativa* plant.
41. Method of obtaining a *Lactuca sativa* plant resistant against *Bremia lactucae*, comprising:
   a. obtaining a F1-hybrid by crossing a *Lactuca saligna* plant with a *Lactuca sativa* plant, which is sensitive to infestation with *Bremia lactucae*;
   b. backcrossing the F1-hybrid with said *Lactuca sativa* plant; and
   c. identifying a plant resulting from the cross exhibiting resistance to *Bremia lactucae* and comprising at least one marker allele co-segregating with said *Bremia* resistance, and
   d. optionally, growing said plant.
42. Method for obtaining seed according to any of the preceding embodiments comprising the steps of:
   a. obtaining a first *Lactuca sativa* plant according to any one of the preceding embodiments;
   b. crossing said first *Lactuca sativa* plant with a second *Lactuca sativa* plant, wherein said second *Lactuca sativa* plant lacks said allele; and
   c. identifying a plant resulting from the cross exhibiting resistance to *Bremia lactucae* and comprising at least one marker allele co-segregating with said *Bremia* resistance; and
   d. harvesting progeny seed from said cross comprising at least one marker allele co-segregating with said *Bremia* resistance.
43. A method according to any one of embodiments 40 to 42, wherein in step c) a plant resulting from the cross and comprising the *Bremia* resistance locus is identified in a PCR reaction by amplification of a DNA fragment with a pair of PCR oligonucleotide primers selected from
a. primer pair 1 represented by a forward primer of SEQ ID NO: 1 and a reverse primer of SEQ ID NO: 2,
b. primer pair 2 represented by a forward primer of SEQ ID NO: 3 and a reverse primer of SEQ ID NO: 4,
c. primer pair 3 represented by a forward primer of SEQ ID NO: 5 and a reverse primer of SEQ ID NO: 6;
d. primer pair 4 represented by a forward primer of SEQ ID NO: 7 and a reverse primer of SEQ ID NO: 8; and
e. primer pair 5 represented by a forward primer of SEQ ID NO: 9 and a reverse primer of SEQ ID NO: 10; or by any other marker on chromosome 8 that is statistically correlated and thus genetically linked to the *Bremia* resistance trait.

44. A method according to embodiment 43, wherein for the amplification product of primer pair 1 and primer pair 2, respectively, the fragment size is determined.

45. A method according to embodiment 43, wherein the SNP co-segregating with the *Bremia* resistance locus is determined, comprising the additional step of using a probe molecule selected from the group consisting of SEQ ID NO: 11, SEQ ID NO: 13 and SEQ ID NO: 15.

46. A method according to any one of embodiments 40 to 42, wherein in step c) the plant resulting from the cross is identified by applying phenotypic selection based on the plants exhibiting an increased resistance to *Bremia lactucae*.

47. A method according to any one of embodiments 40 to 42, wherein in step c) the plant resulting from the cross is identified by applying the combined steps of using a PCR reaction according to any one of embodiments 43, and a phenotypic selection according to embodiment 46.

48. Method of protecting a *Lactuca sativa* plant against infestation with *Bremia lactucae*, comprising
a. obtaining a *Lactuca sativa* plant resistant to *Bremia lactucae* according to any one of embodiments 1 to 23; and
b. growing said plant in an area with high disease (*Bremia lactucae*) pressure.

49. Use of a seed according to any one of embodiments 26 to 30 for growing a Lactuca sativa plant resistant to *Bremia lactucae*.

The invention claimed is:

1. A *lactuca sativa* plant resistant to *Bremia Lactucae* resistance locus is linked to a genetic determinant from the genome of wild *Lactuca saligna* plant, wherein said *Bremia lactucae* resistance locus is a qualitative locus located on linkage group 8, and wherein said *Bremia lactucae* resistance locus is present in *Lactuca sativa* line LSA-(1306/SAT× SAT)-37-1-3:1, a representative seed of said line deposited under Accession No. NCIM 41625.

2. The plant according to claim 1, wherein the *Bremia lactucae* resistance locus is genetically linked to at least one marker locus, which co-segregates with the *Bremia lactucae* resistance trait and can be identified in a PCR reaction comprising the amplification of a DNA fragment with a pair of PCR oligonucleotide primers selected from the group consisting of:

a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6,
   d. primer pair 4 represented by a forward primer of SEQ ID NO: 7 and a reverse primer of SEQ ID NO: 8, and e. primer pair 5 represented by a forward primer of SEQ ID NO: 9 and a reverse primer of SEQ ID NO: 10.

3. The plant of claim 2, wherein primer pair 1 and primer pair 2 each amplifies an SSR fragment which co-segregates with the *Bremia lactucae* resistance locus, wherein;
   a. primer pair 1 amplifies an SSR fragment of 247 bp;
   b. primer pair 2 amplifies an SSR fragment of 465 bp;
   c. primer pair 3 amplifies a DNA fragment within the 247 by SSR fragment comprising an SNP which segregates with the *Bremia* resistance locus wherein said SNP comprises a C for A nucleotide exchange at position 272 in the SSR sequence; and
   d. primer pair 4 and primer pair 5 each amplifies a DNA fragment within the 465 by SSR fragment, wherein said SNP comprises a G for A nucleotide exchange at position 430 and a T for G nucleotide exchange at position 305 in said SSR fragment.

4. A seed from the plant of claim 2, a representative sample of said seed is deposited under Accession No. NCIMB 41625.

5. A method of detecting in a *Lactuca sativa* plant the presence of a DNA marker that is linked to the *Bremia lactucae* resistance locus, said method comprising: a) obtaining DNA from said plant; b) obtaining a pair of PCR oligonucleotide primers selected from the group consisting of:
   i. primer pair 1 represented by a forward primer of SEQ ID NO: 1 and a reverse primer of SEQ ID NO: 2,
   ii. primer pair 2 represented by a forward primer of SEQ ID NO: 3 and a reverse primer of SEQ ID NO: 4,
   iii. primer pair 3 represented by a forward primer of SEQ ID NO: 5 and a reverse primer of SEQ ID NO: 6,
   iv. primer pair 4 represented by a forward primer of SEQ ID NO: 7 and a reverse primer of SEQ ID NO: 8, and
   v. primer pair 5 represented by a forward primer of SEQ ID NO: 9 and a reverse primer of SEQ ID NO: 10; c) performing a PCR reaction comprising DNA of step a) and primers of step b); and d) analyzing the results; wherein the *Bremia lactucae* resistance locus is a qualitative locus located on chromosome 8.

6. A method for introducing at least one allele associated with resistance to *Bremia lactucae* at a qualitative trait locus contributing to resistance to *Bremia* into a *Lactuca sativa* plant lacking said allele comprising:
   a. obtaining a first *Lactuca sativa* plant according to claim 2;
   b. crossing said first *Lactuca sativa* plant with a second *Lactuca sativa* plant, wherein said second *Lactuca sativa* plant lacks said allele; and
   c. identifying a plant resulting from the cross exhibiting increased resistance to *Bremia lactucae* and comprising at least one marker allele co-segregating with said *Bremia* resistance.

7. A method of obtaining a *Lactuca sativa* plant resistant against *Bremia lactucae*, the method comprising:
   a. obtaining a F1-hybrid by crossing a *Lactuca saligna* plant with a *Lactuca sativa* plant, which is sensitive to infestation with *Bremia lactucae*;
   b. backcrossing the F1-hybrid with said *Lactuca sativa* plant; and
   c. identifying a plant resulting from the cross exhibiting resistance to *Bremia lactucae* and comprising at least one marker allele co-segregating with said *Bremia* resistance; wherein said marker allele is NL0918 or NL0920 linked to *Bremia lactucae* qualitative resistance locus on chromosome 8.

8. The method according to claim 6, wherein c) a plant resulting from the cross and comprising the *Bremia lactucae* resistance locus is identified in a PCR reaction comprising the amplification of a DNA fragment with a pair of PCR oligonucleotide primers selected from the group consisting of
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10.

9. The plant of claim 2, wherein said plant is homozygous for the *Bremia lactucae* resistance locus.

10. The plant of claim 2, wherein said plant is *Lactuca sativa* line LSA-(1306/SAT×SAT)-37-1-3:1, a representative seed of said line deposited under Accession No. NCIM 41625 comprises a genetic background of NCIMB 41625.

11. A *Bremia lactucae* resistant plant generated from the method as described in claim 6, wherein the *Bremia lactucae* resistance locus is a qualitative locus located on chromosome 8.

12. A *Bremia lactucae* resistant plant generated from the method as described in claim 7, wherein the *Bremia lactucae* resistance locus is a qualitative locus located on chromosome 8.

13. A *Bremia lactucae* resistant plant generated from the method as described in claim 8, wherein the *Bremia lactucae* resistance locus is a qualitative locus located on chromosome 8.

14. The method of claim 6, wherein step c) comprises the amplification of a DNA fragment with a pair of PCR oligonucleotide primers selected from the group consisting of
   a. primer pair 1 represented by a forward primer of SEQ ID NO: 1 and a reverse primer of SEQ ID NO: 2,
   b. primer pair 2 represented by a forward primer of SEQ ID NO: 3 and a reverse primer of SEQ ID NO: 4,
   c. primer pair 3 represented by a forward primer of SEQ ID NO: 5 and a reverse primer of SEQ ID NO: 6;
   d. primer pair 4 represented by a forward primer of SEQ ID NO: 7 and a reverse primer of SEQ ID NO: 8; and
   e. primer pair 5 represented by a forward primer of SEQ ID NO: 9 and a reverse primer of SEQ ID NO: 10.

15. A *Bremia lactucae* resistant plant generated from the method as described in claim 14, wherein the *Bremia lactucae* resistance locus is a qualitative locus located on chromosome 8.

16. A seed that produces the plant of claim 2.

* * * * *